United States Patent [19]

Godek et al.

[11] Patent Number: 5,399,678
[45] Date of Patent: Mar. 21, 1995

[54] PROCESS FOR SULTAMICILLIN INTERMEDIATE

[75] Inventors: Dennis M. Godek, Glastonbury; Thomas A. Morris, Groton, both of Conn.

[73] Assignee: Pfizer Inc., New York, N.Y.

[21] Appl. No.: 927,288

[22] PCT Filed: Mar. 15, 1991

[86] PCT No.: PCT/US91/01765
§ 371 Date: Sep. 28, 1992
§ 102(e) Date: Sep. 28, 1992

[51] Int. Cl.$^6$ ............................................. C07D 499/00
[52] U.S. Cl. ............................................................ 540/310
[58] Field of Search ........................ 540/310, 311, 312

[56] References Cited

U.S. PATENT DOCUMENTS

| | | | |
|---|---|---|---|
| 4,244,951 | 1/1981 | Bigham | 424/250 |
| 4,342,772 | 8/1982 | Godtfredsen et al. | 424/271 |
| 4,381,263 | 4/1983 | Jasys | 260/239 |
| 4,704,456 | 11/1987 | Adams | 540/310 |
| 4,942,229 | 7/1990 | Seeki et al. | 540/310 |

FOREIGN PATENT DOCUMENTS

| | | |
|---|---|---|
| 0061284 | 3/1982 | European Pat. Off. |
| 0095341 | 5/1983 | European Pat. Off. |
| 0108545 | 10/1983 | European Pat. Off. |
| 0382863 | 2/1989 | European Pat. Off. |
| 1139584 | 6/1989 | Japan |
| 2044255 | 1/1980 | United Kingdom |

OTHER PUBLICATIONS

Binderup, E., et al., Chlorosulfates as Reagents in the Synthesis of Carboxylic Acid Esters Under Phase--Transfer Conditions; Synthetic Communications, 14(9), 857–865 (1984).

*Primary Examiner*—Nicholas Rizzo
*Attorney, Agent, or Firm*—Peter C. Richardson; Gregg C. Benson; A. Dean Olson

[57] ABSTRACT

A simplified method for making the chloromethyl ester of sulbactam in which the tetraalkylammonium sulbactam salt is not dried and isolated prior to alkylation. The method comprises reacting a tetraalkylammonium salt and a sulbactam salt in an aqueous solution to form an aqueous solution of tetraalkylammonium sulbactam. The tetraalkylammonium sulbactam is extracted into bromochloromethane or iodochloromethane, and water is removed from the organic layer to enhance the formation of the chloromethyl ester of sulbactam. The tetraalkylammonium sulbactam is reacted with bromochloromethane or iodochloromethane in the organic layer to form the chloromethyl ester of sulbactam.

9 Claims, No Drawings

PROCESS FOR SULTAMICILLIN INTERMEDIATE

This was filed under 35 U.S.C. § 371 based on PCT/US91/01765 filed on Mar. 15, 1991 which was a continuation of U.S. application Ser. No. 07/509,256, now abandoned, which was filed on Apr. 13, 1990.

TECHNICAL FIELD

The field of art to which this invention relates are methods of making haloalkyl esters of sulbactam.

BACKGROUND ART

The present invention is concerned with an improved method of preparing the chloromethyl ester of sulbactam

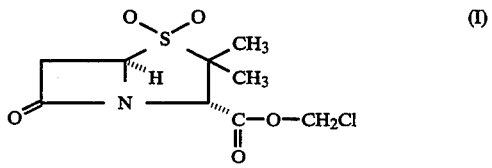

a key intermediate in the manufacture of sultamicillin. See Bigham, U.S. Pat. Nos. 4,244,951 and Godfredsen et al., 4,342,772. Sulbactam and sultamicillin are the U.S.A.N. (U.S. Adopted Names) or generic names for penicillanic acid 1,1-dioxide and for the mixed methandiol ester with sulbactam/ampicillin, respectively.

The preparation of the ester intermediate of the formula (I) in high yield and quality by reaction of the carboxylate salt of the formula

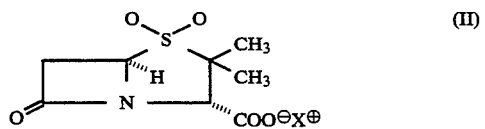

wherein $X^+$ is a metal or ammonium cation, with chloroiodomethane or bromochloromethane suffers from the problem that the product is contaminated by the bis-ester of the formula

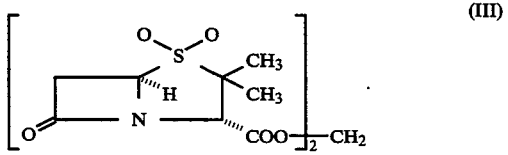

The use of the salt of formula II, wherein X is tetrabutylammonium, by Jasys, commonly assigned U.S. Pat. No. 4,381,263, the disclosure of which is hereby incorporated by reference, improved the yield of the desired ester (I), but even here appreciable bis-ester (III) was formed [Binderup et al. Synthetic Communications, vol. 14, pages 857–864 (1984)].

More recently, Binderup et al. have employed chloromethyl chlorosulfate in place of chlorobromomethane or chloroiodomethane in reaction with the tetrabutylammonium salt of formula (II). Although the level of bis-ester is reduced thereby, use of chloromethyl chlorosulfate requires specialized equipment and handling for plant scale operations.

Commonly assigned U.S. Pat. No. 4,704,456 teaches a further variation for making the chloromethyl ester of sulbactam. That patent teaches the addition of, for example, tert-amines to improve the rate of chloromethyl ester formation, and the yield of the chloromethyl ester I (at the expense of the bis-ester (III)).

Although there are a variety of processes for producing the chloromethyl ester of sulbactam there is a continuing search in this field of art for more efficient high yielding processes.

SUMMARY OF THE INVENTION

This invention is directed to a simplified method for making the chloromethyl ester of sulbactam in which the step of drying and isolating the tetraalkylammonium sulbactam salt is eliminated. The method comprises reacting a tetraalkylammonium salt and a sulbactam salt in an aqueous solution to form an aqueous solution of tetraalkylammonium sulbactam. The tetraalkylammonium sulbactam is extracted into bromochloromethane or iodochloromethane, and water is removed from the organic layer to enhance the formation of the chloromethyl ester of sulbactam. The tetraalkylammonium sulbactam is reacted with bromochloromethane or iodochloromethane in the organic layer to form the chloromethyl ester of sulbactam.

DETAILED DESCRIPTION OF THE INVENTION

Any metal (e.g. potassium, sodium, or calcium) salt of sulbactam may be utilized as a starting material for this process, however the sodium salt is preferred. In addition, the free acid may also be used.

A wide variety of tetraalkylammonium salts can be used. However, it is preferred to use a tetrabutylammonium salt (e.g. tetrabutylammonium hydrogen sulfate, tetrabutylammonium hydroxide) as the sulbactam tetrabutylammonium salt (II) is readily extracted with the halochloromethanes described below.

Bromochloromethane or iodochloromethane is used as both the tetraalkylammonium sulbactam salt extraction solvent and the alkylating reagent for the making of the chloromethyl ester of sulbactam. Generally an excess is used to reduce the formation of the unwanted bisesters (III). Due to cost, stability, and better recoverability, chlorobromomethane is preferred over chloroiodomethane. Optionally a reaction-inert, water-immiscible cosolvent such as methylene chloride or ethyl acetate may be added. As used herein, the expression "reaction inert solvent" refers to those solvents which do not interact with starting materials, intermediates or products in a manner which adversely affects the yield of the desired product.

Any drying agent that is effective in achieving the desired chloromethyl ester of sulbactam may be used in this process, however it is preferred to use a sulfate salt because of its ready availability and effectiveness. Exemplary compounds include $CaSO_4$, $Na_2SO_4$, $MgSO_4$ trihydrate and $MgSO_4$, of which $MgSO_4$ is preferred. Any amount of the drying agent that is effective in minimizing the amount of the unwanted bis-ester described in the Background Art may be used. By minimizing is meant reducing to less than about 10%. Typically about 50 to about 200 (wt sulfate salt/wt 30 metal sulbactam salt) % drying agent is used as these amounts are effective and above 200% effectiveness is not improved. In addition organic drying agents such as propylene carbonate, ethylene carbonate, acetic anhydride, or methyl formate may be used. In addition drying agents such as molecular sieves (synthetic zeolites) may be used. Suitable molecular sieves are #3A 8–12 mesh available from Aldrich Co. (Milwaukee, Wis.).

Generally the process of this invention comprises reacting the sulbactam salt and the tetraalkylammonium salt in an aqueous solution, extracting the tetraalkylammonium sulbactam salt with bromochloromethane or iodochloromethane and reacting the tetraalkylammonium sulbactam salt and halochloromethane while removing water in situ by either adding a drying agent or azeotropically, without first removing water from the organic layer, isolating the tetraalkylammonium sulbactam salt and drying it.

Preferably the tetraalkylammonium sulbactam salt is formed at a pH such that the salt is not decomposed (i.e. stable). It is especially preferred that the pH is about 4 to about 8 because above about 8 the beta-lactam ring may hydrolyze and below about 4 the free acid of the tetraalkylammonium salt may form. The pH is typically adjusted by addition of a base such as NaOH.

Any concentration of sulbactam salt that is effective in achieving the desired end product may be used, however preferably about 10 to about 30 (wt gm tetraalkylammonium sulbactam salt/vol ml water) % concentration is used as this facilitates the extraction of the sodium tetrabutylammonium salt from the aqueous layer into bromochloromethane.

Any temperature may be used that does not adversely affect forming the sulbactam tetrabutylammonium salt, however typically the temperature is from about 15° C. to about 40° C. Typically the pressure is about ambient and the reaction is effectively instantaneous.

Preferably the drying agent is added to the water wet organic sulbactam tetraalkylammonium salt solution layer of the above described extraction. Alternatively water may be removed azeotropically (e.g., simple distillation, fractional distillation) from the water wet organic sulbactam tetraalkylammonium salt solution layer of the above described salt solution. Any concentration of sulbactam salt that is effective in achieving the desired end product may be used, however, preferably about 50 to about 1000 mole equivalents (halochloromethane/sulbactam tetraalkylammonium salt) concentration is used because above about 1000 mole eq. no advantage is gained and below about 50 mole eq. more of the unwanted bis-ester may form. Typically the pH is not adjusted. Any temperature may be used that does not adversely affect the production of the chloromethyl ester of sulbactam, however it is preferred that the temperature be from about 25° C. to about 80° C. because above about 80° C. the chloromethyl ester may degrade and below about 25° C. undesired amounts of the bis-ester may form. The time is a function of a number of parameters such as temperature and pressure however, typically the reaction takes about 2 hours to about 8 hours time. Typically the pressure is about ambient but the reaction may be run at reduced pressure, particularly when azeotropically removing the water. In addition the reaction may be performed at elevated pressures (e.g. up to 20 p.s.i.).

EXAMPLE 1

Chloromethyl penicillanic acid 1,1-dioxide

No drying agent present.

Tetrabutylammonium hydrogen sulfate (41.6 g) was dissolved in 138 ml water at 20°–25° C., and the pH was adjusted to 7.0 with sodium hydroxide. To this solution was charged 25.0 g penicillanic acid 1,1-dioxide sodium salt, which resulted in complete solution after brief stirring and the addition of 1–3 ml water. The aqueous solution was extracted 3×218 ml each bromochloromethane. The extractions were monitored by optical rotation, which suggested that only 0.5% of material remained in the aqueous layer after the third extraction. The organic layers were combined, an additional 640 ml bromochloromethane were added, and the reaction was stirred at 22°–25° C. in the absence of light. The reaction progress was monitored by high pressure liquid chromatography (HPLC), and the following in situ results were obtained.

| Time (hrs) | % Product | % Bis ester |
|---|---|---|
| 4.25 | 30.7 | |
| 5.0 | 35.2 | |
| 6.25 | 41.0 | |
| 9.0 | 51.0 | |
| 23.0 | 66.8 | 11.9 |

The reaction was washed 3×300 ml with water, and the organic layer was vacuum concentrated to a volume of 520 ml. The remaining bromochloromethane was displaced with a total of 800 ml isopropanol to a final volume of 600 ml. A slurry developed which was granulated 1 hour at 20°–25° C., filtered, washed with cold isopropanol, and vacuum dried giving 12.8 g of white material which assayed for 74.9% product and 20.6% of the bis ester. A second crop of material was isolated (6.0 g) which assayed as 89.7% product. The total isolated assayed yield was 54.2%.

EXAMPLE 2

Chloromethyl penicillanic acid 1,1-dioxide

Magnesium sulfate drying agent present.

The tetrabutylammonium salt of sulbactam was prepared and extracted with bromochloromethane as in Example 1. To the wet bromochloromethane solution was added 10 g magnesium sulfate, and the solution was reacted and monitored as above.

| Time (hrs) | % Product | % Bis ester |
|---|---|---|
| 4.0 | 57.1 | |
| 5.0 | 61.4 | 6.8 |
| 6.0 | 67.5 | 6.8 |
| 7.0 | 70.1 | 7.9 |

The reaction was generally worked-up as in the first example. Two crops of material were again isolated. The first crop (14.6 g) assayed as 84.7% product, and the second crop (5.2 g) assayed as 90.4% sulbactam chloromethyl ester. The isolated assayed yield for this reaction was 62.1% product and 6.6% bis ester.

EXAMPLE 3

Chloromethyl penicillanic acid 1,1-dioxide

Repeat of Example 2 at higher temperature.

The preparation and extraction of the tetrabutylammonium sulbactam salt was followed as in Example 1. Magnesium sulfate was added as in Example 2, and the solution was reacted at 28° C. The wet bromochloromethane solution was sampled (10 ml) before adding the magnesium sulfate, and both the reaction and sample were stirred at 28° C.

| | Time (hrs) | % Product | % Bis ester |
|---|---|---|---|
| Reaction w/MgSO4 | 4.0 | 72.0 | 8.5 |
| 10 ml sample, No drying agent | 4.25 | 40.5 | |
| | 6.0 | 52.5 | |

After reacting the main portion 4.25 hours with drying agent, the reaction was washed 3×300 ml each water, vacuum concentrated to a volume of ~500 ml, displaced with 800 ml isopropanol to a volume of ~350 ml, stirred 30 minutes at ambient temperature and then 1 hour at 5° C. The white slurry was isolated by filtration, the cake washed with cold isopropanol, and vacuum dried giving 20.9 g of material. The assay of this material was 89.9% product and 8.3% of the bis ester. The filtrate contained another 6.5% product and 0.5% bis ester. The isolated yield for this reaction was 68.2%.

EXAMPLE 4

Chloromethyl penicillanic acid 1,1-dioxide

Reaction with 5×'s the amount of magnesium sulfate as in Example 3.

Tetrabutylammonium hydrogen sulfate (16.6 g) was dissolved in 55 ml water with stirring at ambient temperature. The pH was adjusted to neutral with sodium hydroxide, 10 g sodium sulbactam was charged, and the pH was readjusted to neutral with base while adding 5 ml water. The aqueous tetrabutylammonium sulbactam solution was extracted 3×88 ml each with bromochloromethane, the extracts were combined and combined with an additional 260 ml bromochloromethane (the waste stream or "raffinate" could be used in Example 11). Magnesium sulfate (20 g) was charged, and the reaction was stirred at 26°-30° C. The reaction was monitored by HPLC.

| Time (hrs) | % Product | % Bis ester |
|---|---|---|
| 2.0 | 77.1 | 7.6 |
| 2.5 | 80.2 | 10.1 |

After 3.5 hours, the reaction was washed 6×120 ml each with water, and then the organic layer was vacuum concentrated a 150 ml volume. This solution was displaced with 400 ml isopropanol and concentrated to a final volume of 70 ml. A slurry developed, which was held cold for 12 hours, then the white material was isolated by filtration. The dried weight was 9.2 g which assayed for 85.7% product and a yield of 73.1%. The amount of the bis ester was 8.6%. The filtrate contained 4.7% product and 0.8% of the dimer.

EXAMPLE 5

Chloromethyl penicillanic acid 1,1-dioxide

Reaction with less bromochloromethane (150 mole equivalents) and approximately the same amount of magnesium sulfate as in Example 4.

The reaction conditions were followed as in Example 4, and the HPLC results were the following.

| Time (hrs) | % Product | % Bis ester |
|---|---|---|
| 1.25 | 63.7 | 5.8 |
| 2.5 | 74.8 | 10.0 |

| Time (hrs) | % Product | % Bis ester |
|---|---|---|
| 3.5 | 76.8 | 11.9 |

EXAMPLE 6

Chloromethyl penicillanic acid 1,1-dioxide

Reaction using more bromochloromethane (250 mole equivalents) and the same amount of magnesium sulfate as in Example 4.

The reaction conditions were followed as in Example 4, and the HPLC results were the following.

| Time (hrs) | % Product | % Bis ester |
|---|---|---|
| 1.0 | 55.3 | 2.4 |
| 2.5 | 76.8 | 6.5 |
| 3.5 | 80.0 | 13.2 |
| 4.0 | 80.3 | |

EXAMPLE 7

Chloromethyl penicillanic acid 1,1-dioxide

Molecular sieves as the drying agent.

Tetrabutylammonium hydrogen sulfate (8.3 g) was dissolved in 27.5 ml water at ambient temperature, and adjusted to neutral pH with sodium hydroxide. Sodium sulbactam (5.0 g) was charged, and the pH was readjusted to neutral with more base. The aqueous tetrabutylammonium sulbactam salt solution was extracted 3×44 ml each bromochloromethane. The extractions were combined with an additional 130 ml bromochloromethane, 8.5 g of 3A molecular sieves were added, and the reaction was stirred at 26°-28° C. while being monitored by HPLC. The in situ assays were as follows.

| Time (hrs) | % Product | % Bis ester |
|---|---|---|
| 3.0 | 65.0 | 6.7 |
| 4.0 | 69.0 | 8.6 |

EXAMPLE 8

Chloromethyl penicillanic acid 1,1-dioxide

Reaction with calcium sulfate as drying agent.

Reaction conditions were identical to those in Example 4. The in situ HPLC results were as follows.

| Time (hrs) | % Product | % Bis ester |
|---|---|---|
| 2.5 | 69.8 | 5.7 |
| 3.5 | 74.6 | 8.3 |
| 4.5 | 76.9 | 10.3 |

EXAMPLE 9

Chloromethyl penicillanic acid 1,1-dioxide

Reaction with sodium sulfate as the drying agent.

The tetrabutylammonium salt was prepared as in Example 4, and the chloromethylation reaction was run on one half of the bromochloromethane solution with 2 g sodium sulfate as the drying agent at 28°-35° C.

| Time (hrs) | % Product | % Bis ester |
| --- | --- | --- |
| 2.25 | 41.8 | 2.5 |
| 3.25 | 50.7 | 3.8 |

EXAMPLE 10

Reaction with 50 mole equivalents bromochloromethane.

The tetrabutylammonium sulbactam salt was prepared as in Example 4, extracted from the aqueous layer 1×30 ml bromochloromethane and 1×34 ml bromochloromethane (50 mole equivalents total). The organic layers were combined, 10 g magnesium sulfate was added, and the reaction was stirred at 28°–30° C. The reaction was monitored by HPLC which showed the following results.

| Time (hrs) | % Product | % Bis ester |
| --- | --- | --- |
| 1.0 | 59.0 | 12.6 |
| 2.0 | 66.2 | 22.0 |
| 3.0 | 63.5 | 25.5 |

EXAMPLE 11

Reaction with tetrabutylammonium sulfate recycle.

The chloromethylation reaction was run as in Example 4, and the chloromethyl ester of sulbactam yield from this reaction was 80.0%. The bromochloromethane layer, after the chloromethylation reaction, was washed with water, and the aqueous wash was passed through an anion-exchange resin column on the hydroxyl cycle. The solution was neutralized, combined with the original sulbactam/tetrabutylammonium aqueous raffinate, and concentrated. This resulted in formation of two layers. The top tetrabutylammonium sulfate layer was recycled in the process of Example 4, and the chloromethyl ester of sulbactam yield with the recycled material was 80.0%.

EXAMPLE 12

Chloromethyl penicillanic acid 1,1dioxide (CME)

Methylformate Drying Agent

Tetrabutylammonium hydrogen sulfate (33.28 grams) was dissolved in 110.4 milliliters of water and the pH adjusted to 7.0–7.5 with approximately 26 milliliters of 4N sodium hydroxide. To this was charged 20 grams of penicillanic acid 1,1-dioxide sodium salt and the pH readjusted to 7.0–7.5 with 0.2N sodium hydroxide. The resulting aqueous solution was extracted 3×190 milliliters of bromochloromethane. The organic layers were combined and made up to 1048 milliliters with additional bromochloromethane. To this solution was added 13.75 milliliters of methylformate. The reaction was heated to 50° C. The reaction was monitored by high performance liquid chromatography, with the following results:

| Reaction Time (minutes) | Stoichiometric Yield CME |
| --- | --- |
| 50 | 78.9 |
| 60 | 81.0 |
| 70 | 81.9 |
| 80 | 82.0 |

The reaction was not isolated.

The above experiment was repeated, yielding a maximum yield after 80 minutes of 77.4%.

EXAMPLE 13

Chloromethyl penicillanic acid 1,1-dioxide (CME)

Azeotropic Distillation Drying Approach

City water (110.4 milliliters) and tetrabutylammonium hydrogen sulfate (33.28 grams) were stirred in a flask until dissolved. The pH was adjusted to 7.18 using 4N sodium hydroxide. Penicillanic acid 1,1-dioxide sodium salt (20 grams) was added and the pH readjusted to 7.21 with sodium hydroxide. After 30 minutes stir the pH was 7.2. The resulting water solution was extracted with bromochloromethane (3×189.2 milliliters) and the extracts made up to 1080 cc with additional bromochloromethane. With the reactor equipped with condensor and Dean-Stark tube capable of recycling the bottom layer, the following conditions were applied to the system: pot temperature (25°–31° C.); vacuum (∼140–145 mm). After 1½ hours, 3 milliliters of water had been removed and after 2 hours the reaction was then water washed and the washed bromochloromethane layer reassayed using a very accurate volume measurement. This yield was 80%.

The reaction was not isolated.

EXAMPLE 14

1,000 Equivalents Bromochloromethane (BCM) 66° and 50° C. MgSO$_4$ drying

Tetrabutylammonium hydrogen sulfate (6.66 grams) and 22.1 ml of water were added to a flask. The pH was adjusted to 7.0–7.5 with 5.2 ml of 4N sodium hydroxide. 4.0 grams of penicillanic acid 1,1-dioxide sodium salt (98.6% purity) were added to the flask and the pH was adjusted to 7.0–7.5 with 0.2N sodium hydroxide. The resulting solution was extracted with 3×38 ml of bromochloromethane and the extracts combined.

934 ml of BCM were added to another flask and warmed to 66° C. The above extracts were added to the BCM and then 8.0 grams of magnesium sulfate were added to the flask. After ten minutes the yield maximized at 97.8% by high performance liquid chromatography.

When the above was repeated at 50° C., the yield maximized at 98.4% after fifty minutes.

This invention provides an improved, efficient method of making the chloromethyl ester of sulbactam. Surprisingly, the alkylation reaction with bromochloromethane (which is an aqueous sensitive reaction) proceeds without prior aqueous drying and isolation of the tetraalkylammonium sulbactam salt. In fact, the addition of a suitable drying agent to the water wet solution of the tetraalkylammonium sulbactam salt or azeotropic water removal results in equivalent or better reaction rates and yields than when the tetraalkylammonium sulbactam salt is first dried and isolated.

Thus, this invention makes a significant contribution to the field of manufacturing sultamicillin by providing more efficient method of making the chloromethyl ester of sulbactam. The process does not require a separate step to remove water and isolate the sulbactam salt, the alkylation proceeds quicker and provides equivalent or better yields of the monoester with concurrently lower formation of the undesired bisester.

It should be understood that the invention is not limited to the particular embodiments shown and described herein, but that various changes and modifications may be made without departing from the spirit and scope of this novel concept as defined by the following claims.

We claim:

1. A method for making the chloromethyl ester of sulbactam comprising:
   a) contacting a tetraalkylammonium salt and a sulbactam salt in an aqueous solution to form an aqueous solution of tetraalkylammonium sulbactam;
   b) combining said aqueous solution of tetraalkylammonium sulbactam and bromochloromethane or iodochloromethane to form an aqueous and an organic layer;
   c) separating said layers;
   d) removing water from said organic layer to enhance the formation of the chloromethyl ester of sulbactam; and
   e) allowing said tetraalkylammonium sulbactam to react with the bromochloromethane or iodochloromethane, in said organic layer, to form the chloromethyl ester of sulbactam.

2. The method as recited in claim 1 wherein the sulbactam salt is sodium sulbactam.

3. The method as recited in claim 1 wherein the tetraalkylammonium salt is tetrabutylammonium hydrogen sulfate.

4. The method as recited in claim 1 wherein said water is removed by the in situ addition of a drying agent.

5. The method as recited in claim 1 wherein the drying agent is $MgSO_4$ or methylformate.

6. The method as recited in claim 1 wherein the water is removed azeotropically.

7. The method as recited in claim 1 wherein the aqueous solution of tetraalkylammonium sulbactam salt is formed at a pH of about 4 to about 8.

8. The method as recited in claim 4 wherein about 50 to about 1000 mole equivalents bromochloromethane or iodochloromethane is used.

9. The method as recited in claim 1 wherein bromochloromethane is used.

* * * * *